United States Patent
Thomas et al.

(10) Patent No.: US 9,212,976 B2
(45) Date of Patent: Dec. 15, 2015

(54) VISION-GUIDED ASPIRATION APPARATUS AND METHODS

(71) Applicant: QIAGEN GAITHERSBURG, INC., Gaithersburg, MD (US)

(72) Inventors: Bradley Scott Thomas, Timonium, MD (US); Edward Medri, Gaithersburg, MD (US); Carl Theodore Edens, Highland, MD (US); Brian Austin Self, Monkton, MD (US)

(73) Assignee: Qiagen Gaithersburg, Inc., Gaithersburg, MD (US)

( * ) Notice: Subject to any disclaimer, the term of this patent is extended or adjusted under 35 U.S.C. 154(b) by 426 days.

(21) Appl. No.: 13/840,708

(22) Filed: Mar. 15, 2013

(65) Prior Publication Data

US 2014/0260699 A1    Sep. 18, 2014

(51) Int. Cl.
*G01N 1/14* (2006.01)
*G01N 1/28* (2006.01)
*G01N 35/10* (2006.01)

(52) U.S. Cl.
CPC ............ *G01N 1/286* (2013.01); *G01N 35/1011* (2013.01); *G01N 2035/1025* (2013.01)

(58) Field of Classification Search
None
See application file for complete search history.

(56) References Cited

U.S. PATENT DOCUMENTS

| | | | |
|---|---|---|---|
| 2,461,623 A | 2/1949 | Armerding | |
| 3,050,239 A | 8/1962 | Williams, Jr. | |
| 4,472,357 A | 9/1984 | Levy et al. | |
| 4,650,883 A * | 3/1987 | Holland et al. | 549/312 |
| 4,997,632 A | 3/1991 | Rodewald | |
| 5,024,933 A | 6/1991 | Yang et al. | |
| 5,187,102 A * | 2/1993 | Stocker et al. | 436/69 |
| 5,310,527 A | 5/1994 | Romanauskas et al. | |
| D356,232 S | 3/1995 | Armstrong et al. | |
| 5,846,493 A | 12/1998 | Bankier et al. | |
| D445,907 S | 7/2001 | Monks | |
| 6,336,358 B1 * | 1/2002 | Kishimori et al. | 73/61.65 |
| 6,673,595 B2 | 1/2004 | Barbera-Guillem | |
| 6,796,195 B2 | 9/2004 | Povey et al. | |
| 7,405,036 B2 | 7/2008 | Loskutoff et al. | |
| 7,523,649 B2 | 4/2009 | Corey et al. | |
| 7,543,480 B2 | 6/2009 | Africk et al. | |
| D608,013 S | 1/2010 | Coulling et al. | |

(Continued)

FOREIGN PATENT DOCUMENTS

WO    WO 89/07255    8/1989

OTHER PUBLICATIONS

International Search Report for PCT International Application No. PCT/US13/65869 dated Mar. 19, 2014.

(Continued)

*Primary Examiner* — Robert R Raevis
(74) *Attorney, Agent, or Firm* — RatnerPrestia

(57) ABSTRACT

A method for removing supernatant from a sample tube. The method includes providing a sample tube having a pellet at a bottom of the sample tube and a supernatant liquid above the pellet, visually inspecting the sample tube to determine one or more geometric properties of the pellet, and determining an expected height of a top surface of the pellet based on the one or more geometric properties determined in the visual inspection step. The method also includes inserting an aspirator into the supernatant liquid, moving the aspirator downwards towards the expected height of the top surface of the pellet, and aspirating the supernatant liquid through the aspirator.

24 Claims, 5 Drawing Sheets

(56) References Cited

U.S. PATENT DOCUMENTS

| | | |
|---|---|---|
| 7,739,911 B2 | 6/2010 | Panetta |
| D621,521 S | 8/2010 | Nuotio |
| 7,838,296 B2 | 11/2010 | Corey et al. |
| 8,031,918 B2 | 10/2011 | Roth |
| 2004/0152129 A1 | 8/2004 | Garey et al. |
| 2007/0177778 A1 | 8/2007 | Massaro |
| 2007/0194043 A1 | 8/2007 | Mank et al. |
| 2009/0075340 A1 | 3/2009 | Padkaer et al. |
| 2009/0103772 A1 | 4/2009 | Baumfalk et al. |
| 2009/0275076 A1 | 11/2009 | Knesel et al. |
| 2010/0029710 A1 | 2/2010 | Bigge et al. |
| 2010/0253771 A1 | 10/2010 | Bae et al. |
| 2011/0287948 A1 | 11/2011 | Suresh et al. |
| 2012/0083598 A1 | 4/2012 | Suh et al. |
| 2012/0196344 A1 | 8/2012 | Li et al. |

OTHER PUBLICATIONS

International Search Report and Written Opinion for PCT International Application No. PCT/US2014/026022 dated Jul. 18, 2014.
Office Action for U.S. Appl. No. 13/657,705 dated Sep. 30, 2014.
International Search Report for PCT International Application No. PCT/US13/065869 dated May 7, 2015.

* cited by examiner

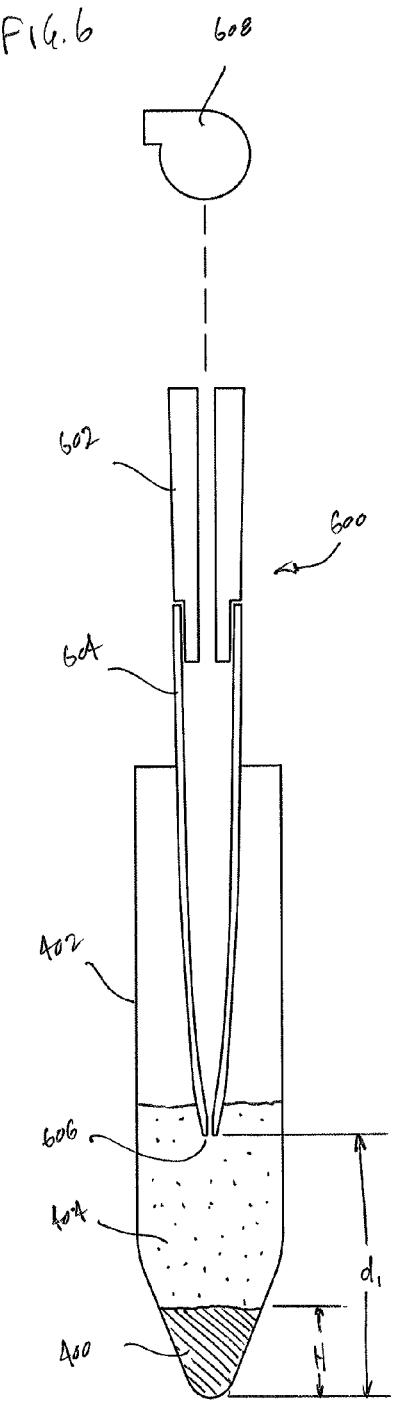
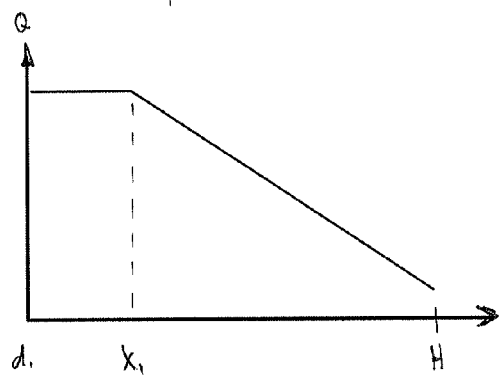
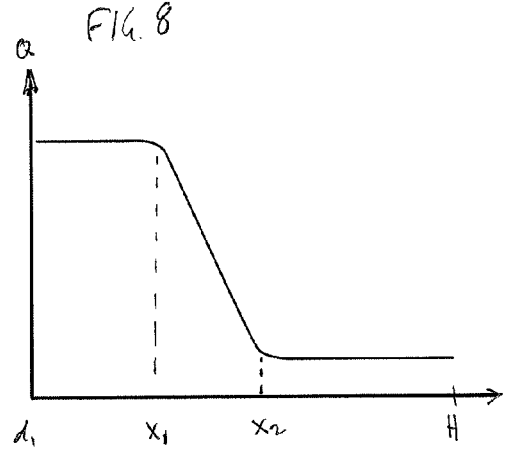

US 9,212,976 B2

VISION-GUIDED ASPIRATION APPARATUS AND METHODS

BACKGROUND OF THE INVENTION

1. Field of the Invention

The present invention relates to automated systems and methods for processing samples, such as biological samples. Particular exemplary embodiments relate to removing supernatant from sample vials using vision-guided aspiration apparatus and methods.

2. Description of the Related Art

Automated sample processing systems may include a variety of devices and subsystems intended to perform a number of different processing steps on the samples being processed. In many instances, devices are provided to remove liquid from a sample container. Pipettors and aspirators, which use suction to remove liquids, are commonly used for this purpose. In some cases, such as in U.S. application Ser. No. 13/657,633 entitled "Automated Pelletized Sample Decanting Apparatus and Methods," which is incorporated herein by reference, liquid may be removed by overturning the container to decant the liquid. In other cases, the sample container may include a permeable or openable bottom surface that allows liquid to elute or drain out of the container.

While many different kinds of existing liquid removing systems are used, such systems may have certain limitations or drawbacks. In particular, when the liquid to be removed is a supernatant that is in the same container as a solid or pelletized sample, in some cases it may be difficult or impossible to use a conventional device to accurately remove the supernatant without disturbing or removing the sample, and in such cases it may be necessary to remove the supernatant manually, which can be time-consuming and relatively expensive. Furthermore, devices that can remove supernatant without disturbing the sample may only be able to do so when the sample is accurately positioned at a particular location, or when the sample has particular dimensions or other properties. For example, a pipettor that is programmed to descend to a predetermined height to aspirate supernatant may operate well when the pellet is one size, but leave surplus supernatant in the container if the pellet is smaller than expected, or aspirate some or all of the pellet if the pellet is larger than expected. As another example, devices that decant the liquid may operate effectively and accurately regardless of the pellet size, but may require a relatively large space commitment and include multiple relatively complex moving parts.

The foregoing problems may exist in a variety of processing systems. As one example, processing systems that are intended to perform steps of the QIAGEN Hybrid Capture® 2 ("HC2") nucleic acid hybridization assay may need to remove supernatant from a pelletized sample. In the HC2 protocol, the sample may be provided in vials containing either the PreservCyt® preservative fluid (available from QIAGEN Gaithersburg, Inc. of Gaithersburg, Md.), the SurePath™ preservative fluid (available from Becton, Dickinson and Company of Franklin Lakes, N.J.), or other fluids. In the HC2 process, the sample may be mixed and aliquoted to a sample processing container, such as a 10 milliliter Sarstedt conical tube or a 15 milliliter VWR or Corning brand conical tube, or an automated processing tube strip. Sample conversion buffer (e.g., 0.4 milliliters added to 4.0 milliliters of specimen for 1-2 tests per sample) is added to the processing tube, and then the tube is capped and thoroughly mixed using a vortex mixer with a cup attachment. Next, the tube is centrifuged in a swinging bucket rotor at 2,900 ($\pm$150)$\times$g for 15 ($\pm$2) minutes, to form a sample pellet. In the manual process, the operator visually verifies that there is a pellet in the tube. If there is a pellet, the operator manually decants the supernatant by inverting the tube and gently blotting (approximately 6 times) on absorbent low-lint paper towels until liquid no longer drips from the tube. Each blot is done on a clean area of the towel. During blotting, the operator observes the tube to ensure that the cell pellet does not slide down the tube. Details and other processing steps of the HC2 protocol (both in manual and automated form) are provided in U.S. application Ser. No. 13/657,633.

To automate the HC2 protocol, it is necessary to separate the supernatant from the pelletized sample. U.S. application Ser. No. 13/657,633 provides a decanting system to perform this task, but alternative solutions may be desirable for a variety of reasons. Similarly, it may be desirable to provide alternative mechanisms and procedures for other processes that require a liquid to be removed from a solid sample, and particularly a pelletized sample.

SUMMARY

In one exemplary embodiment, there is provided a method for removing supernatant from a sample tube. The method includes providing a sample tube having a pellet at a bottom of the sample tube and a supernatant liquid above the pellet, visually inspecting the sample tube to determine one or more geometric properties of the pellet, and determining an expected height of a top surface of the pellet based on the one or more geometric properties determined in the visual inspection step. The method also includes inserting an aspirator into the supernatant liquid, moving the aspirator downwards towards the expected height of the top surface of the pellet, and aspirating the supernatant liquid through the aspirator.

The recitation of this summary of the invention is not intended to limit the claims of this or any related or unrelated application. Other aspects, embodiments, modifications to and features of the claimed invention will be apparent to persons of ordinary skill in the art in view of the disclosures herein.

BRIEF DESCRIPTION OF THE DRAWINGS

A better understanding of the exemplary embodiments may be understood by reference to the attached drawings, in which like reference numbers designate like parts. The drawings are exemplary and not intended to limit the claims in any way.

FIG. 6 is schematic front view of an aspirating system being used with a tube and pellet.

FIG. 7 is a plot flow rate versus distance for one exemplary aspirating process.

FIG. 8 is a plot flow rate versus distance for another exemplary aspirating process.

DETAILED DESCRIPTION

The exemplary embodiments described herein relate to automated sample processing apparatus and methods. In general terms, the described exemplary embodiments are used to remove liquid from a sample container that includes both a pelletized sample and the liquid to be removed. Automated processes for performing this step may use multi-axis motion of the container to decant the supernatant in a manner that approximates a manual decanting process. The embodiments described herein may provide a more easily automated substitute for such decanting processes, and other benefits may be apparent from the present disclosure and practice of the inventions. The embodiments are described herein in the context of removing supernatant from a pelletized sample created during an HC2 protocol, but these and other embodiments may be used, with or without adaptation, in other processes.

Figure 1:
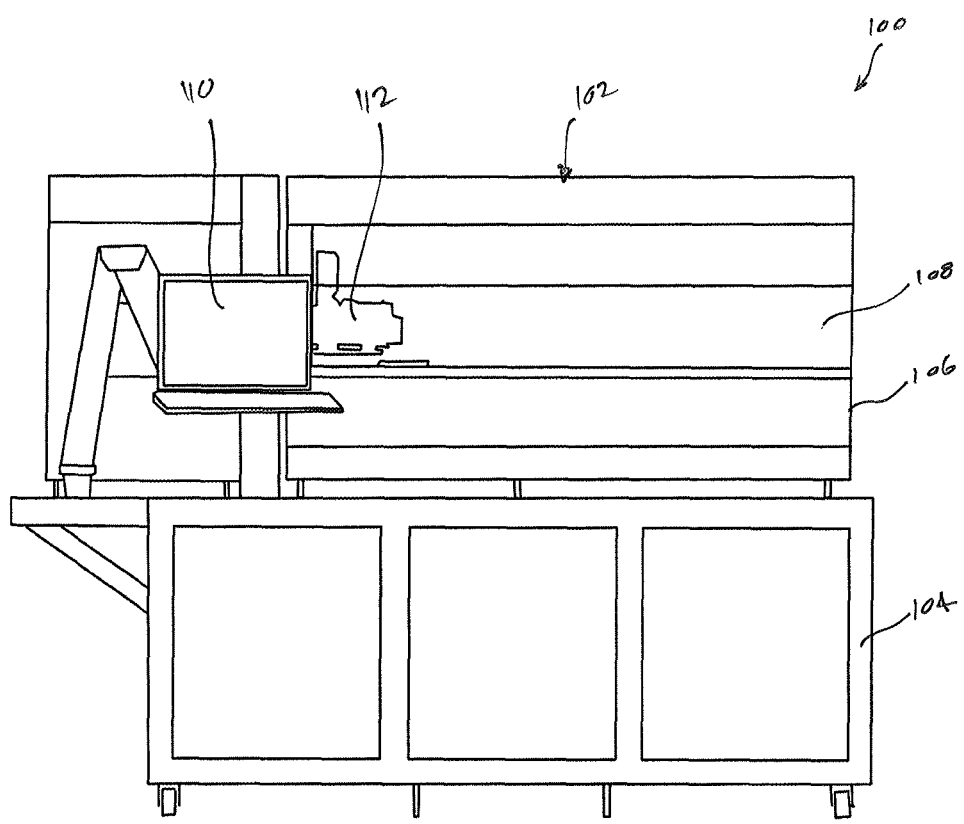
FIG. 1 is a front view of an exemplary sample preparation apparatus.

An exemplary embodiment of an automated sample preparation apparatus 100 is illustrated in FIG. 1. In general terms, the apparatus 100 includes a processing module 102 that may be mounted on a stand 104. The processing module 102 may contain some or all of the operating parts, storage facilities for supplies, and so on. The stand 104 may include additional components, such as a power supply, reagent supplies, consumable supplies, and the like. The stand 104 may be incorporated into the processing module 102 to form a large processing module 102, but alternatively the processing module 102 may be operationally independent of the stand 104 so that the processing module 102 can be used as a table-top unit. The processing module 102 preferably includes a housing 106, having one or more openable covers, such as a transparent front panel 108. Suitable lockout systems may be provided to prevent operation when the housing 106 is open. The apparatus 100 may also include a computer processing unit ("CPU"), which may be integrated into the processing module 102, located in a remote or separate processor such as an external computer 110, or distributed over a network of communicating processors. The CPU may be operatively connected to a variety of robotic devices located in the processing module 102, such as pipettors 112, transport mechanisms, heaters, optical equipment, shakers, barcode readers, and the like.

Figure 2:
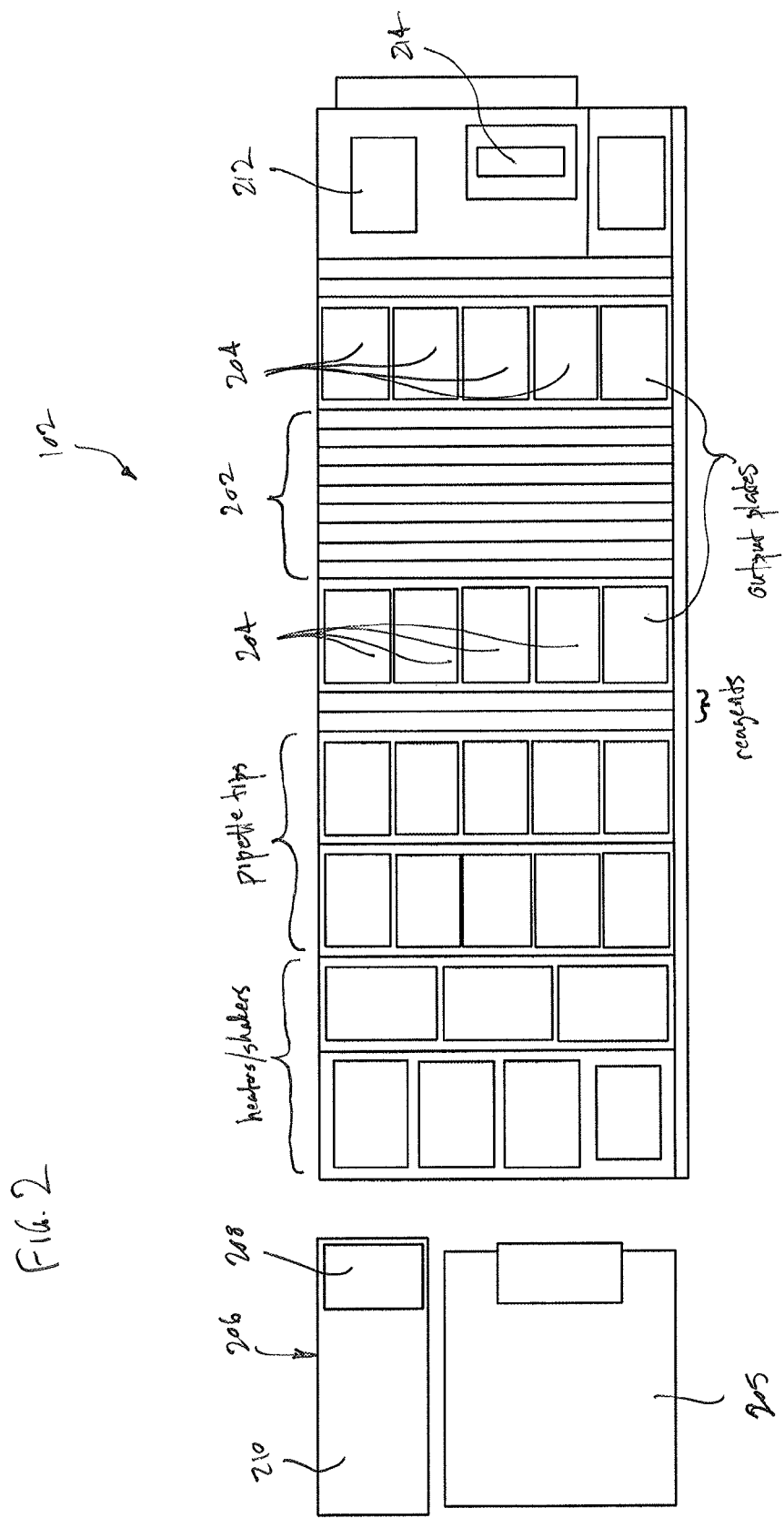
FIG. 2 is a schematic plan view of an exemplary processing module.

Referring to FIG. 2, an exemplary processing module 102 is illustrated in schematic plan view. In general terms, the exemplary processing module 102 performs a visual inspection of the samples, and uses this inspection to aspirate a quantity of liquid from each sample container. The processing module also may perform various steps of a processing protocol, such as an automated HC2 protocol, as described in U.S. application Ser. No. 13/657,633.

The illustrated exemplary processing module 102 is configured for performing an automated HC2 protocol. The processing module 102 includes a sample input station 202, which may be loaded with supplies of tube strips loaded into tube strip racks, individual sample containers, or the like. The tube strips or individual samples tubes may be transferred to holders 204 for convenient bulk processing through the processing module 102. The holder 204 may comprises a frame that holds individual containers or tube strips in a two-dimensional array of rows (e.g., a 4×6 array of individual tubes, or six 4-tube strips), or a multi-well plate having integral wells that directly hold each sample.

In the HC2 protocol, the samples are provided in tubes that are centrifuged (e.g., at approximately 2,900 gravities for approximately 15 minutes) to form a pelletized sample below a supernatant liquid. The processing module 102 may include a centrifuge to perform this pellet formation step, but in alternative embodiments the samples may be pelletized prior to being loaded into the processing module 102. In other processes, the sample may start as a supernatant liquid having a solid object that does not require pelletization.

The processing module 102 also includes a vision inspection system 206 having an inspection station 208 and a camera system 210. The inspection station 208 is configured to successively receive each holder 204 during the inspection process, but may alternatively be configured to receive individual sample containers. The processing module 102 also includes an aspiration station 212 that successively receives each holder 204 during the aspiration process. The aspiration station 212 may include an aspiration waste receptacle 214 comprising any suitable fluid receptacle or drain system. Details and functions of the vision inspection system 206 and aspiration station 212 are provided below.

Suitable robotic handling equipment is provided to move the holders 204 through the processing module 102, and to and from the inspection station 208 and aspiration station 212. For example, automated material handling systems, such as the pipette channels, autoloaders, iSWAP microplate grippers, and CO-RE grippers in the STAR Line of robotics provided by Hamilton Robotics of Reno, Nev., may be used to move the holders 204 and perform other functions. Other features, such as safety locks, lights, ventilation or seals, consumable supplies, and the like, may be included in or with the processing module 102, as desired for the particular application.

Figure 3:
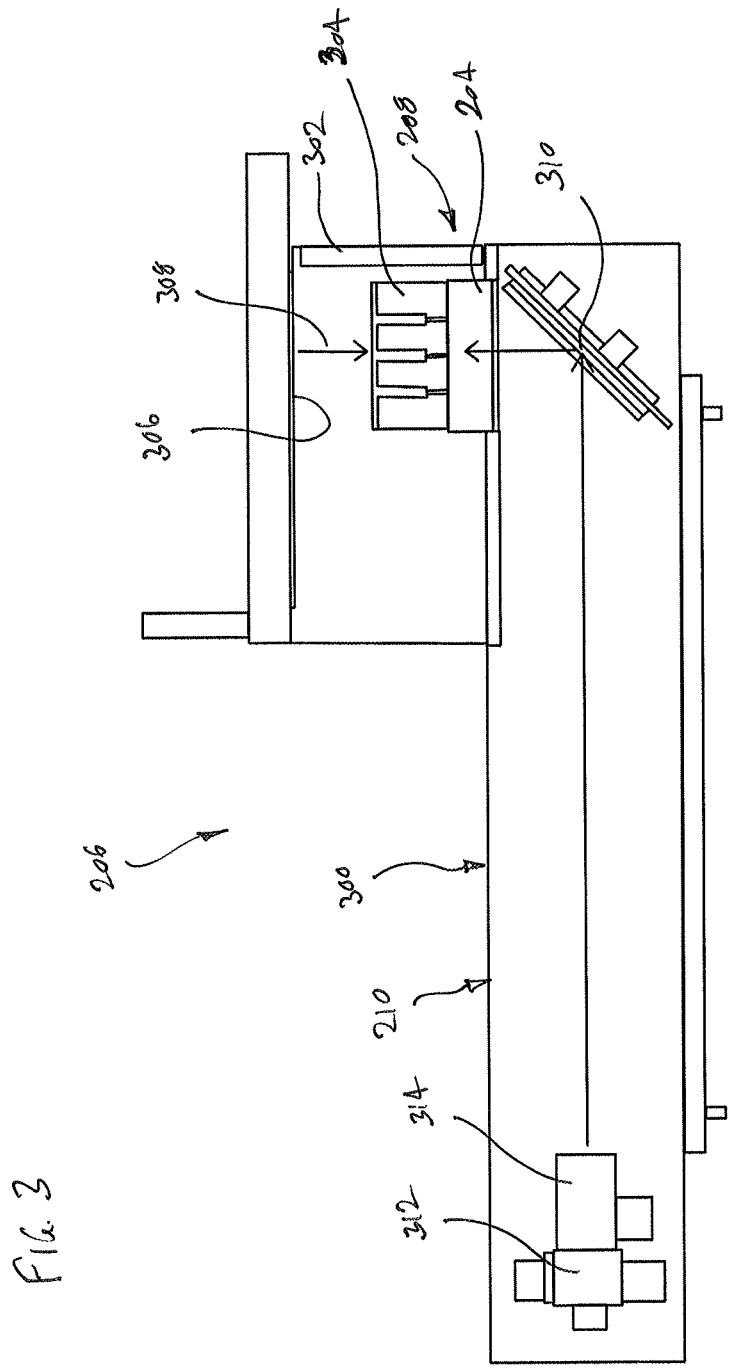
FIG. 3 is a front view of an exemplary vision inspection system.

The vision inspection system 206 may comprise any system capable of generating an image of the sample in the sample container. An example of a vision inspection system 206 is illustrated in FIG. 3. This vision inspection system 206 includes an inspection station 208 and a camera system 210 located inside a common housing 300. The inspection station 208 is accessed through an opening that may be selectively covered by a movable door 302. To prevent ambient light from possibly affecting the inspection process, the housing 300 (and door 302, if provided) preferably block or reduce the intrusion of ambient light into the housing 300 when the door 302 is closed. The door 302 may be operated by any suitable actuator, such as a simple motor or the like. As shown in FIG. 3, the holder 204 rests in the inspection station 208, preferably holding a number of sample containers 304 in an upright position.

A light source 306 is located above the inspection station 208 to illuminate the containers 304 and the samples therein. The light source 306 may comprise one or more light-emitting diodes ("LEDs"), fluorescent or incandescent bulbs, or other devices to generate camera-visible light. The light source 306 preferably generates a relatively homogenous pattern of parallel or at least diffuse emitted light 308, and may include one or more diffusers to eliminate local bright spots that might affect the inspection results. The emitted light 308 may be monochromatic to mitigate chromatic aberrations and other phenomena that might affect the inspection process, but this is not strictly required in all embodiments, and white or otherwise mixed light may be suitable in other embodiments. The emitted light 308 also may be within the human-visible wavelength, but this also is not strictly required, as cameras can be adapted to detect human-invisible wavelengths.

In the shown embodiment, the tubes 304 preferably are at least partially transparent to the wavelength(s) of light used for the inspection. Materials such as natural polypropylene homopolymer, molded polystyrene, and others, may possess sufficient optical clarity to permit the necessary imaging. If it is desired to minimize optical refraction as the light passes through the liquid and tube material, the refractive indices of the tube and liquid may be matched or approximately matched. For example, for liquids high in alcohol, which has a relatively low refractive index, a material such as NEOFLON™ EFEP RP-4040 (an ethylene tetrafluoroethylene based polymer available from Daikin Industries, Ltd. Of Osaka, Japan) may possess a refractive index that is close to that of the liquid, thereby reducing or minimizing refraction. Other materials may be selected, if desired or necessary, for other liquid media.

The inspection station 208 may be located between the light source 306 and a mirror 310 located below the inspection station 208. The emitted light 308 thus generates a silhouette image of the tube contents that reflects off the mirror 310. Suitable light masks may be provided to prevent errant reflections of the light beam 308 from confusing or obscuring the silhouette image. The mirror 308 preferably is sized to reflect the silhouettes of all of the tubes 304 without having to, reposition the mirror 308 or other parts, which allows all of the samples to be inspected simultaneously.

The mirror 310 directs the silhouette image to a camera 312 and lens 314. As used herein, the term "camera" includes conventional camera devices having exposed film or one or more image sensors to detect and record an image, or any other device or array of detectors suited to receive and record an image. For example, the camera may comprise a digital camera system having one or more charged-couple device ("CCD") or complementary metal-oxide-semiconductor ("CMOS") sensors. One example, of a camera is a 5 megapixel color detector coupled to a 23 millimeter high-resolution lens. The camera may be adapted to detect a particular wavelength of human-visible or human-invisible light, or a spectrum covering multiple wavelengths. Associated processing software may be used to capture the silhouette image for each holder 204, generate on-screen or printed images of the silhouette, and so on. Machine vision cameras and software suitable for use as inspection systems 206 are commercially available from a variety of sources, and need not be described herein.

The imaging layout in the embodiment of FIG. 3 is expected to provide relatively clear images of pellets in the tubes 304. In this configuration, the camera views the tubes 304 and pellets from the bottom, which helps reduce the optical influence of the liquid column located above the pellet. Diffusion or distortion of the light that might be caused by the liquid column occurs essentially before the light passes around the pellet, which minimizes the influence of such phenomena on the pellet image. In contrast, if the positions of the camera 312 and light source 306 are reversed, light traveling around the pellet continues through the liquid column before reaching the camera 312. In this reversed arrangement, the liquid column may reduce the contrast of the pellet as compared to the rest of the scene, and the water column's meniscus may act as a lens to distort the image. Nevertheless, alternative embodiments may use a camera above the tubes 304 if the contrast reduction and distortion are minimized, accounted for using processing algorithms or empirical studies, or determined to be insignificant. The upward-looking and downward-looking orientations both allow simultaneous examination of all of the pellets and tubes in a two-dimensional array.

Other arrangements, such as placing both the light source 306 and the camera 312 either above or below the tubes may be used in other embodiments. In still other embodiments, the camera 312 and light source 306 may be placed on the sides of the tube, to directly examine the height of the pellet. As still another embodiment, the light source 306 may be omitted if it is not necessary under the circumstances. Also, the mirror 310 may be omitted and the camera 312 placed directly below the inspection station 208. Also, filters and other optical devices (e.g., focusing lenses and the like) may be added in other embodiments. Other variations and modifications will be apparent to persons of ordinary skill in the art in view of the present disclosure.

Figure 4:
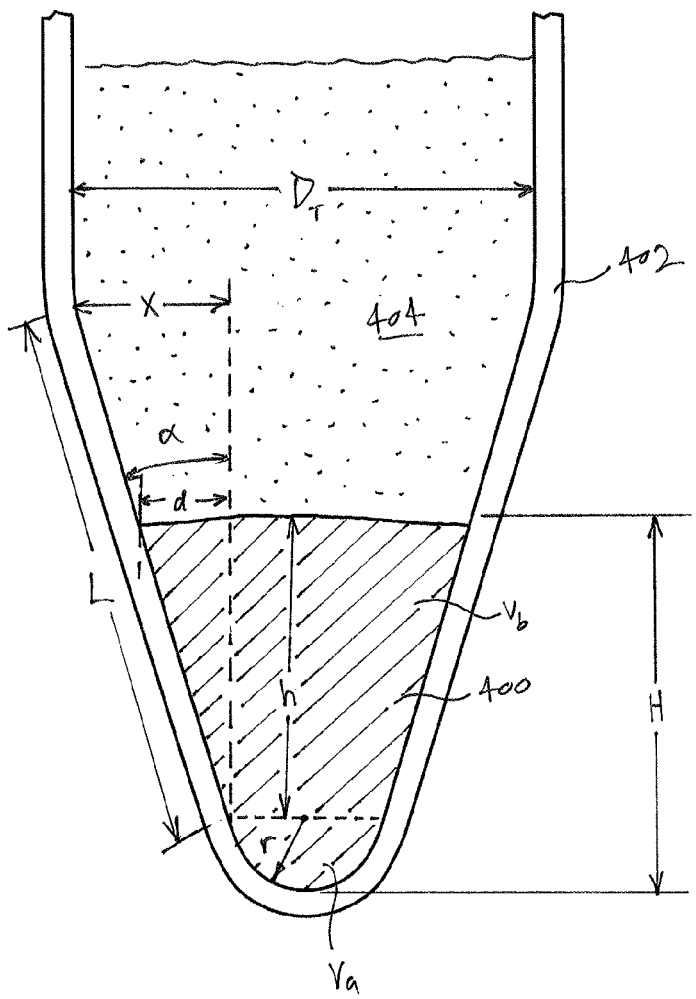
FIG. 4 is a cutaway front view of an exemplary tube and pellet.

The vision inspection system 206 evaluates each pelletized sample to determine one or more geometric properties that are relevant to the subsequent aspiration process. FIG. 4 illustrates an example of a pellet 400 that is formed in the bottom of a tube 402. The tube 402 has a conical lower end at the bottom of a cylindrical sidewall (a common construction for centrifuge tubes). The tube 402 may have cone geometry matching a conventional 10-milliliter Sarstedt tube, such as the tubes used in a manual HC2 protocol. In typical centrifuging operations, particularly those performed in the HC2 protocol, the large centrifuge forces create a sample pellet 400 at the bottom of the tube 402. The pellet 400 occupies only a portion of the conical volume, and typically has a flat or somewhat rounded upper surface. Supernatant liquid 404 fills the portion of the tube 402 immediately above the pellet 400. The objective of the aspiration process is to remove as much of the supernatant liquid 404 as practical, in order to minimize any influence this liquid 404 may have on subsequent processing steps and test results. As such, the physical dimension of primary concern is the total height of the pellet 400. In the embodiment of FIG. 4, the total height "H" is the sum of dimension "h" and dimension "r". If desired, a correction factor or buffer distance may be added to the value determined as "H". For example, empirical studies may yield a distance expected to prevent ingestion of the pellet 400 into the pipettor 600 or to prevent contact between the pellet 400 and the pipettor 600 during normal operating conditions (e.g., conditions within a six sigma statistical range of experimental samples).

Figure 5:
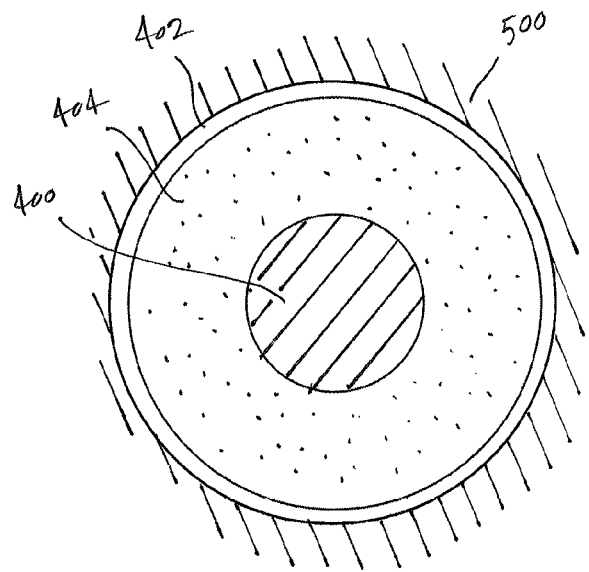
FIG. 5 is a cutaway top view of the exemplary tube and pellet of FIG. 4.

An example of a bottom view of a single tube/pellet image is shown in FIG. 5. This image would be part of an array of similar images if multiple tubes and pellets are examined at once. Regions between adjacent tube locations preferably are blocked by a mask 500 that blocks potentially-disruptive light from interfering with the pellet image. The mask 500 also may provide a reference dimension for assessing the size of the pellet. It will be appreciated that the bottom view as shown in FIG. 5 may not provide a direct indication of the pellet's height. However, the pellet's maximum diameter D may be measured by comparing the size of the pellet's silhouette to a reference scale, such as the mask's diameter, or the like. The vision inspection system 206 may use contrast-enhancing algorithms, blob finding algorithms, or other known data processing methods to measure linear dimensions, calculate the area of the pellet, estimate the diameter (as may be necessary if the pellet's silhouette is not a regular geometric shape), and so on. Such algorithms and processes are known in the art of machine vision systems and need not be detailed herein. Other algorithms, such as for detecting the presence of a pellet and accounting for artifacts in the image (e.g., a dark ring caused by light bending through the transition between the conical lower wall and hemispherical tip of the tube), may be used as well. Examples of such algorithms are provided in U.S. application Ser. No. 13/657,633.

Once the pellet's maximum diameter D is measured or calculated, this value can be used to determine the total height H of the pellet 400. The total height H may be calculated using known dimensions of the tube 402, or by reference to a lookup table that correlates diameter values to height values for a given type of tube 402. Expected distortion caused by the light passing through the tube 402 may be accounted for in the calculations or lookup tables. Where calculations are performed, the pellet height H is readily calculated as the sum of the radius r of the hemispherical bottom of the tube 402, and the height h of the conic frustum located above the hemispherical bottom. In this case, the frustum height h may be calculated using trigonometric equations; specifically, $h=d/(\tan \alpha)$, where $d=(D/2)-r$, and $\alpha$ is the known angle of the conical portion of the tube. Similar equations may be used to calculate the volume of the pellet 400, which is equal to the volume of the hemispherical region (i.e., $V_a=(2/3)\pi r^3$) plus the volume of the frustum (i.e., $V_b=(\pi h/3)((D/2)^2+(D/2)r+r^2)$). Other geometric properties also may be determined using the simple measurement of the diameter D, and other equations may be derived to account for alternative tube 402 shapes (e.g., a flat bottomed tube may use a different set of equations or lookup table). As noted, however, a simple lookup table may be generated to correlated measured values of the pellet diameter D to other geometric dimensions, based on calculations or empirical studies. Lookup tables, and empirical studies to correlate the pellet's maximum diameter D to other geometric properties such as the total pellet height H, may be particularly useful if the tubes 402 have an irregular or non-geometric shape that is not amenable to efficient or rapid mathematical calculations.

In alternative embodiments in which the vision inspection system 206 examines the side profile of the pellet 400 and tube 402, it may be possible to directly measure the total height H of the pellet 400. Such a system may be convenient for systems that process single tubes or one-dimensional rows of tubes, but may not be possible or efficient for a two-dimensional array of tubes. In a side-view system, it may necessary to account for distortion caused by light passing through the conical tube surface, but such will be possible to a person of ordinary skill in the art without undue experimentation in view of the teachings in the present disclosure. A side-view system also may use fixed features, such as a thickness of the tube or some other feature, as reference dimensions. If tubes 402 having different shapes are processed simultaneously, each tube may be analyzed differently according to predetermined criteria, and the locations of the different tubes can be readily tracked using barcode scanning and the like.

The geometric data that is collected or generated for each pellet 400 in the array of tubes 402 is placed into an electronic record to associate this data (or at least the most relevant aspects of the data, such as the pellet height) with each particular sample tube 402. This data is used to control the aspiration process as described below.

Following vision inspection, the samples are moved to the aspiration station 212. The aspiration station 212 includes one or more aspirating devices, such the pipettor 600 shown in FIG. 6. The exemplary pipettor 600 includes a suction channel 602 and a disposable tip 604. The suction channel 602 is mounted to a conventional robotic system that is able to move the pipettor 600 up and down to aspirate the supernatant liquid 404. In systems that progressively move each tube 402 under the pipettor 600, it may only be necessary to move the pipettor 600 up and down. It is more preferred, however, to also provide drive equipment (e.g., motors and tracks) to move the pipettor 600 laterally, which facilitated the process of picking up and disposing of disposable pipette tips 604, and expelling removed supernatant liquid 404 at a remote location such as an aspiration waste receptacle 214. If the pipettors 112 are provided as ganged pipettor channels (e.g. a four-channel pipettor), as known in the art, each channel preferably can be moved in the vertical direction independently of the other channels. The pipette tip 604 releasably mounts to the bottom of the suction channel 602, and preferably is sized to remove the desired volume of fluid without allowing the fluid to reach and contaminate the channel 602.

Pipetting systems are well-known in the art, and any conventional programmable pipetting system may be used for this purpose. For example, suitable pipettors may be provided by Hamilton Robotics of Reno, Nev.

The pipettor 600 (or other aspirator) is programmed to use the geometric data obtained using the vision inspection system 206 to aspirate fluid from each sample container. For example, the CPU operating the pipettor 600 uses the location of the pipette opening 606, the location of each tube 402 when the frame 204 is mounted on the aspiration station 212, and the pellet height H, to regulate the position of the pipette opening 606 during the aspiration process.

The location of the pipette opening 606 is a known distance from the end of the suction channel 602, and the location of the suction channel 602 is readily determined using position sensors or by monitoring the robotic drive system. For example, the robotic system may reset to a predetermined "zero" position at regular intervals, and its movements may be controlled using position feedback sensors (e.g., encoder wheels or the like) to constantly monitor the position of the various parts, including the suction channel 602 or the pipette tip 604. Such position tracking is routine and need not be described in more detail herein. If necessary, the pipette tip's manufacturing tolerances and variations in the position of the pipette tip 604 on the suction channel 602 may be incorporated into the determined position of the pipette opening 606 to provide a range of possible locations. Also, a verifying system, such as an optical switch, may be used to ensure that each pipette tip 604 is not longer than expected (e.g., by passing the end of each pipette tip 604 through the optical switch's gap to evaluate whether it is beyond a certain length sufficient to trigger the optical switch).

The location of the top of the each pellet 400 can be determined from the positions of the bottom of each tube 402 when they are placed on the aspiration station 212. The tube positions are readily determined from fixed geometric relations, and the process of programming or "teaching" a robotic system to register the bottom of each tube is a matter of routine robotic system programming that will be apparent to persons of ordinary skill in the art without further explanation herein. Of course, other reference points on the tube 402 may be used in other embodiments. To facilitate more precise operations, the holder 204 may be constructed to precisely mount to the aspiration station 212 so that the tubes 402 are located in their expected position during successive aspiration operations. Similar measures may be taken to ensure that the sample containers, such as tube strips or individual sample containers, are precisely mounted to the holder 204. For example, a clamp (not shown) or other device may hold the sample containers and frame 204 into close contact with the aspiration station 212 during the aspiration process.

Knowing the location of the pipettor opening 606 and the bottom of each tube 402, the CPU can associate the total height H of each pellet 400 with the respective tube 402 to identify the location of the top of each pellet 400. Hence, the CPU can program the pipettor 600 to move the pipettor opening 606 to the desired location relative to the top of each particular pellet 400. With this capability, a variety of control schemes may be used to perform the aspiration process.

A number of variables may be considered when selecting the aspirating process parameters. Preferably, the aspiration process removes a large portion of the liquid 404, but does not remove a significant portion of the pellet 400 or draw the pellet 400 into the pipette opening 606. Factors that can influence the aspiration operation include the minimum size of the gap between the pipette opening 606 and the pellet 400, the aspiration pressure (i.e., negative pressure applied at the pipette opening 606), size of the pipette opening 606, fluid flow rate through the pipette opening 606, properties of the liquid 404 and pellet 400, geometry of the surrounding portion of the tube 402, and so on. The expected tolerances of the pellet measurement and locations of the various parts (pipette opening 606, tubes 602, etc.), which may include manufacturing tolerances and measurement tolerances, also may be considered when establishing the aspiration process parameters, and particularly to reduce the likelihood that variations within such tolerances will complicate or interfere with the process.

In one exemplary embodiment, a CPU may simply move the pipette opening 606 into close proximity to the top of the pellet 400 in a single motion, and begin the aspiration process to withdraw as much liquid 404 as possible from the tube 402. In this case, the minimum gap distance may be based on empirical studies performed a number of samples for a particular pipette opening size, and negative pressure, to determine the minimum gap that will reliably aspirate a sufficient quantity of the supernatant liquid. While such a process may be effective, it is expected that the flow rate may need to be relatively slow to prevent unwanted disturbance of the pellet 400, yielding a relatively slow process.

In another exemplary embodiment, the CPU may be programmed to aspirate the liquid 404 in a two-step process. In the first step, the pipettor 600 starts at or near the top of the liquid column and rapidly moves downward towards the pellet 400 at a high aspiration pressure to a first height $d_1$ above the pellet 400, to quickly remove a first portion of the liquid 404. The first height $d_1$ is selected to be safely above the largest expected pellet height ("H"), and this value may be based on the estimated or calculated measurement of the particular sample pellet 400 being aspirated, on empirical evaluations or testing of a representative number of pellets being processed by the system, or other assumptions or calculations. In the second step, the pipettor 600 moves at a reduced speed, and may be operated at a lower aspiration pressure, as it approaches the height H determined to be the top of the pellet 400 during the vision inspection process (with any included buffer or correction factor). Reducing the speed and aspiration pressure reduces the chances of disturbing or ingesting the pellet 400 during the final descent.

Aspiration may terminate immediately when the pipette tip 606 reaches the expected height H of the pellet, or at an earlier location (e.g. at a fixed distance desired to ensure a gap between the pipette top 606 and the top of the pellet 400). Aspiration also may continue until contact with the pellet 400 is detected using a contact sensor or by identifying an increase in the aspiration pressure. In another embodiment, aspiration may stop when a loss in suction pressure or other means or detected phenomena (e.g., a change in electrical conductivity) indicates a low volume or the absence of supernatant liquid 404. Combinations of the foregoing triggers and other triggers to stop aspiration may be used in other embodiments.

In variations of the foregoing processes, the speed and/or aspiration pressure may be changed in discrete increments, or progressively. For example, the speed and/or aspiration pressure may start at a predetermined peak value, and one or both values may progressively reduce as a function of distance or time as the pipette opening 606 approaches the expected pellet location H. As another example, shown in FIG. 7, the flow rate Q (a function primarily of aspiration pressure), may start and remain at a relatively high constant value until the pipettor reaches a first point $x_1$ above the expected pellet height H, and then constantly reduce as the pipette opening 606 approaches the expected pellet height H. In another example, shown in FIG. 8, the flow rate Q may be constant until the pipette opening 606 reaches a first point $x_1$, then drop progressively until the pipette opening 606 reaches a second point $x_2$, and then remain at a constant value until the pipette tip 606 reaches the expected pellet height H. Other embodiments may immediately drop from the higher flow rate value to the lowest flow rate value, or include multiple intermediate instantaneous or progressive steps. Still other embodiments may aspirate the supernatant while the pipettor 600 is stationary, such as by moving the pipette opening 606 to a fixed location proximal to the expected location of the pellet 400 and starting aspiration once the pipette opening 606 has reached this location. Other variations and modifications will be apparent to persons of ordinary skill in the art in view of the present disclosure.

During the aspirating processes, the pressure in the pipette tip 604, pipette channel 602 or elsewhere may be monitored to assess whether the pressure increases rapidly, indicating the ingestion of the pellet 400 or a clot suspended in the supernatant liquid 404, contact with the pellet 400, or other fault conditions. If a pressure peak is experienced, the pipettor 600 may be operated in reverse to push out the occlusion. Other conventional pipetting systems, such as level detecting systems, also may be used in other embodiments.

Various kinds of pump 608 may be used to operate the pipettor 600 in the foregoing processes. For example, a positive displacement pump may be used to remove the supernatant liquid 404 at a more precise volumetric rate. As another example, a vacuum pump, liquid diaphragm pump, or centrifugal pump may be used for rapid supernatant liquid 404 removal at the expense of some accuracy. A combination of pumps also may be used. For example, a vacuum pump may be used for the first part of a two-step process, and a positive displacement pump used for the final descent to the pellet 400. The provision of hydraulic passages and valves to connect and control such pumps will be understood by persons of ordinary skill in the art and need not be described herein.

It will be appreciated that the foregoing embodiments may be altered or supplemented in various ways. For example, as will be appreciated from the foregoing description, the aspiration station 212 simply requires a location to hold the sample and an aspiration mechanism such as a conventional pipettor. Thus, the aspiration station 212 may serve other purposes, or simply be a predetermined location within the processing module 102. For example, the aspiration station 212 shown in FIG. 2 may be located at the shown starting locations for the frames 204. In any event, attention should be paid to prevent cross-contamination as the fluids are aspirated from each tube and moved to the fluid disposal location.

As shown in FIG. 2, the vision inspection system 206 and decanting station 212 may be incorporated into a processing module 102 having a variety of other equipment. For example, a processing module 102 that is configured for performing an automated HC2 protocol may already use vision inspection equipment to confirm that a pellet is present in a sample container after centrifuging. Such equipment may double as the vision inspection system 206 that evaluates the sample for vision-guided aspiration as described above. In this case, the processes of confirming that a pellet is present and aspirating the supernatant may be combined into essentially a single step. For example, the processor may confirm whether a pellet is present prior to beginning the aspiration process. Alternatively, separate vision inspection equipment may be provided to determine whether a pellet is present and to perform the vision-guided aspiration.

In another embodiment, the aspiration station 212 may be incorporated into the vision inspection station 208 to provide visual feedback during the aspiration process. It is also contemplated that the vision inspection station 208 and aspiration station 212 may be provided as a separate processing module dedicated to performing the vision-guided aspiration procedure on pre-existing samples. Such a device may be configured to receive individual samples and/or samples grouped together on a multi-well plate or other type of holder.

Unless otherwise indicated herein, the volumes and other measurements identified and claimed herein are intended to cover the stated measurement and deviations from the stated measurement that would not be expected by persons of ordinary skill in the art to materially alter the performance of the processes described herein, or that are generally accepted by the relevant persons to be an acceptable error range for the measurement in question. Such deviations would be considered approximations of the stated measurement (e.g., such expected or accepted deviations for a value of 400 microliters would be considered approximately 400 microliters).

The present disclosure describes a number of new, useful and nonobvious features and/or combinations of features that may be used alone or together. The multiple separate inventions stand alone and are not intended to require combination with other inventions. Furthermore, the embodiments described herein are all exemplary, and are not intended to limit the scope of the inventions. It will be appreciated that the inventions described herein can be modified and adapted in various and equivalent ways, and all such modifications and adaptations are intended to be included in the scope of this disclosure and the appended claims.

The invention claimed is:

1. A method for removing supernatant from a sample tube, the method comprising:
   providing a sample tube having a pellet at a bottom of the sample tube and a supernatant liquid above the pellet;
   visually inspecting the sample tube to determine one or more geometric properties of the pellet;
   determining an expected height of a top surface of the pellet based on the one or more geometric properties determined in the visual inspection step;
   inserting an aspirator into the supernatant liquid;
   moving the aspirator downwards towards the expected height of the top surface of the pellet; and
   aspirating the supernatant liquid through the aspirator.

2. The method of claim 1, wherein the pellet comprises a pellet formed during a nucleic acid hybridization assay process.

3. The method of claim 1, wherein visually inspecting the sample tube comprises illuminating the sample tube and capturing an image of the sample tube.

4. The method of claim 1, wherein visually inspecting the sample tube comprises inspecting the sample tube from a location above or below the sample tube.

5. The method of claim 4, wherein the location is below the sample tube.

6. The method of claim 5, wherein visually inspecting the sample tube comprises illuminating the sample tube from a location above the sample tube.

7. The method of claim 4, wherein the one or more geometric properties comprises a diameter of the pellet.

8. The method of claim 7, wherein the visually determining step further comprises determining the diameter of the pellet by comparing an image of the pellet to a reference dimension.

9. The method of claim 7, wherein determining the expected height of the top surface of the pellet comprises identifying a predetermined value associated with the diameter of the pellet.

10. The method of claim 7, wherein determining the expected height of the top surface of the pellet comprises calculating a value based on the diameter of the pellet.

11. The method of claim 1, wherein the steps of moving the aspirator downwards and aspirating the supernatant liquid are performed simultaneously during at least a portion of each step.

12. The method of claim 1, wherein the steps of inserting the aspirator, moving the aspirator downwards, and aspirating the supernatant liquid comprise:
   inserting the aspirator to a first location above the expected height of the top surface of the pellet; and
   aspirating the supernatant liquid at a first flow rate while moving the aspirator towards the expected height of the top surface of the pellet at a first movement rate.

13. The method of claim 12, wherein the first flow rate is constant.

14. The method of claim 12, further comprising terminating the aspirating process when the aspirator reaches a second location above the expected height of the top surface of the pellet.

15. The method of claim 12, further comprising terminating the aspirating process when the aspirator detects contact between the pellet and the aspirator.

16. The method of claim 1, wherein the steps of inserting the aspirator, moving the aspirator downwards, and aspirating the supernatant liquid comprise:
   inserting the aspirator to a first location above the expected height of the top surface of the pellet;
   aspirating the supernatant liquid at a first flow rate while moving the aspirator at a first movement rate to a second location between the first location and the expected height of the top surface of the pellet; and
   aspirating the supernatant liquid at a second flow rate while moving the aspirator at a second movement rate from the second location to the expected height of the top surface of the pellet.

17. The method of claim 16, wherein the first flow rate is constant.

18. The method of claim 17, wherein the first movement rate is constant.

19. The method of claim 16, wherein the first movement rate is constant.

20. The method of claim 16, wherein the second flow rate reduces continuously as the aspirator is moved from the second location to the expected height of the top surface of the pellet.

21. The method of claim 20, wherein the second movement rate reduces continuously as the aspirator is moved from the second location to the expected height of the top surface of the pellet.

22. The method of claim 16, wherein the second movement rate reduces continuously as the aspirator is moved from the second location to the expected height of the top surface of the pellet.

23. The method of claim 1, further comprising monitoring an aspiration pressure during the step of aspirating the supernatant liquid.

24. The method of claim 1, wherein the expected height of the top surface of the pellet includes a buffer or a correction factor.

* * * * *